United States Patent [19]

Morehouse et al.

[11] Patent Number: 4,699,669

[45] Date of Patent: Oct. 13, 1987

[54] LOW D.E. STARCH HYDROLYZATES

[75] Inventors: Alpha A. Morehouse, Muscatine, Iowa; Pamela A. Sander, Hayfield, Minn.

[73] Assignee: Grain Processing Corporation, Muscatine, Iowa

[21] Appl. No.: 829,752

[22] Filed: Feb. 14, 1986

Related U.S. Application Data

[63] Continuation-in-part of Ser. No. 419,218, Aug. 17, 1982, abandoned.

[51] Int. Cl.$^4$ .............................................. C13F 3/00
[52] U.S. Cl. ...................................... 127/30; 435/99; 127/29
[58] Field of Search ................ 127/30, 29, 38, 39, 127/40; 435/99

[56] References Cited

U.S. PATENT DOCUMENTS

| 2,891,869 | 6/1959 | Langlois | 127/38 |
| 3,383,245 | 5/1968 | Scallet et al. | 127/38 |
| 3,756,919 | 9/1973 | Deaton | 127/40 |
| 3,849,194 | 11/1974 | Ambruster et al. | 127/29 |
| 3,853,706 | 12/1974 | Ambruster et al. | 435/99 |
| 4,298,400 | 11/1981 | Ambruster | 435/99 X |

FOREIGN PATENT DOCUMENTS

| 2618131 | 11/1976 | Fed. Rep. of Germany | 127/39 |
| 1274506 | 5/1972 | United Kingdom | 127/38 |

Primary Examiner—Andrew H. Metz
Assistant Examiner—Chung K. Pak
Attorney, Agent, or Firm—Neuman, Williams, Anderson & Olson

[57] ABSTRACT

Low D.E. starch hydrolyzates which can be readily filtered are obtained from non-waxy starches by treatment with bacterial alpha-amylase for an extended period at a temperature above about 95° C.

5 Claims, No Drawings

LOW D.E. STARCH HYDROLYZATES

This application is a continuation-in-part of our copending application, Ser. No. 419,218, filed Sept. 17, 1982, now abandoned.

This invention relates to starch hydrolyzate products and to preparation of such products.

It is known that starch can be hydrolyzed by means of acids or enzymes to produce hydrolyzate products containing sugars and which therefore are useful in foods. The sweetening property of the starch hydrolyzates depends to great extent upon the degree of conversion, that is, the extent to which the starch molecules have been hydrolyzed. A very common method of classifying starch hydrolyzates is to measure the degree of hydrolysis in terms of dextrose equivalent (D.E.) which is a measure of the reducing sugar content of the hydrolyzate calculated as dextrose and expressed as a percentage of the total dry substance. The dextrose equivalent (D.E.) value of a starch hydrolyzate can be determined conveniently by the method of Smogyi, M. described in the Journal of Biological Chemistry 160, 61 (1945) and is the method utilized herein for determining D.E. values.

The use of enzymes for hydrolyzing starch has gained widespread application in recent years and enzymes are employed commercially for manufacturing certain products. Enzymes have an advantage over acid catalysts in that they exhibit specificity for certain linkages. One type of microbial enzyme which is commonly employed is alpha-amylase. Alpha-amylase has the property of splitting 1-4 linkages more or less at random throughout the starch molecule with little effect on the 1-6 linkages. Moreover, alpha-amylase does not readily hydrolyze or split the 1-4 linkage in maltose and maltotriose. Thus, it has been reported that when substantially complete conversion of starch is effected with alpha-amylase, maltose and small amounts of trisaccharides and other lower molecular weight polysaccharides, especially those containing the 1-6 linkages, are present in the final hydrolyzate.

Low D.E. starch hydrolyzates are widely used by the food industry as bodying agents and carriers for food flavors, etc. For many applications the functionality or suitability is enhanced when the D.E. of the hydrolyzate is relatively low. Thus, low D.E. starch hydrolyzates generally exhibit viscosity, film-forming and low sweetness properties which are particularly desired for certain applications. Although the advantages of hydrolyzates with D.E. values less than 10 have been long recognized by the food industry, previous attempts to produce a refined hydrolyzate of non-waxy starch in this D.E. range have been hampered due to the inability to filter the hydrolyzates. Unusual difficulty in filtering such low D.E. products has been a serious problem in the past. Non-waxy low D.E. products have been produced as unrefined hydrolyzates, i.e., unfiltered products, but such products have had limited usage because of incomplete solubility and a marked tendency to become rancid with off flavors and odors during storage.

It is a principal object of the invention to provide novel low D.E. starch hydrolyzates from non-waxy starch.

It is a further object of this invention to provide non-waxy starch hydrolyzates having D.E. values up to about 6 which are bland, colorless and soluble in water.

It is also an object of the invention to provide non-waxy starch hydrolyzates having D.E. values up to about 6 which can be readily filtered, treated with carbon and recovered as refined products in high yields.

It is a still further object of the invention to provide low D.E. non-waxy starch hydrolyzates which produce aqueous solutions of relatively high viscosity, improved emulsion stabilizing properties, improved film strength and good clarity stability.

Another object of the invention is to provide methods for producing novel low D.E. starch hydrolyzates from non-waxy starch.

A further object of the invention is to provide methods for producing non-waxy starch hydrolyzates having D.E. values up to about 6 which are bland, colorless and soluble in water.

An additional object of the invention is to provide methods for producing from non-waxy starch low D.E. hydrolyzates which can be readily filtered and which produce aqueous solutions of relatively high viscosity, improved emulsion stabilizing properties, improved film strength and good clarity stability.

The invention also has as an object the provision of methods for producing non-waxy starch hydrolyzates having D.E. values up to about 6 which can be readily filtered, treated with carbon and recovered as a refined product in high yields.

This invention involves the discovery that low D.E. starch hydrolyzates having D.E. values of about 6 and lower can be produced and filtered and refined by an extended treatment with alpha-amylase at temperatures of about 95° C. and above. In accordance with a presently preferred embodiment of this invention, a non-waxy starch is dispersed in water at a level of 10-40% solids, preferably in the range of 20-30% solids, and liquefied by heating with either acid or a liquefying enzyme as described in U.S. Pat. No. 3,663,369, the disclosure of which is incorporated herein. Whichever method of liquefaction is used, it is important that the liquefaction be carried out so as to provide complete gelatinization with essentially no residual starch granules, with the liquefied starch having a D.E. of not substantially above 3. The pH of the liquefied starch is adjusted to a pH value between about 6.5 and 8.0, preferably between 6.8 and 7.5. Bacterial alpha-amylase is added to the liquefied starch which is adjusted to and maintained at a temperature of about 95° C. or above, preferably at a temperature of about 95°-100° C., for a period of 10 to 60 minutes. When the D.E. is reached, i.e. preferably between 3 and 6, the hydrolyzate is acidified to a pH below 4.5, preferably between 3.5 and 4.0, to inactivate the enzyme, and the hydrolyzate recovered by filtration. The hydrolyzate can then be treated with carbon and dried using procedures common to the art.

The use of an extended treatment with alpha-amylase at temperatures at least about 95° C. is a critical feature of the present invention. Whereas the prior art has taught the use of alpha-amylase at temperatures over 93° C. for brief periods to accomplish liquefaction, the conventional practice has been to reduce the temperature after liquefaction to below 85° C. to maximize the rate of hydrolysis as measured by D.E. increase. Under these conditions the hydrolyzate is essentially unfilterable until the D.E. has reached a value of 8 or higher. We have now discovered that treating the liquefied starch with alpha-amylase at a temperature of 95° C. or higher produces an unexpected improvement in filterability with very little increase in D.E. This discovery, that filterability of hydrolyzates of 6 D.E. and lower is enhanced by extending the time of amylase treatment at 95° C. or above while the rate of D.E. increase is slowed down, is the feature of the present invention which allows the recovery of refined low D.E. hydrolyzates of non-waxy starch which have not previously been available.

A variety of non-waxy starch or amylaceous materials can be employed in accordance with the invention, such as, for example, potato, white sweet potato, grain sorghum, tapioca, wheat, rice, sago and the like. Corn starch is a preferred material.

The type of alpha-amylase suitable for carrying out the present invention is well known to the art and is available commercially under such names as Biocon Canalpha 180, Miles Tenase, or Novo BAN. These are bacterial enzymes produced by *Bacillus subtilis*. Another type of bacterial alpha-amylase which may be used is produced by cultures of *Bacillus licheniformis* and is available commercially under the name Novo Termamyl and Miles Taka-Therm. Amylases derived from *Bacillus licheniformis* have a higher saccharifying activity above 95° C. than amylases derived from *Bacillus subtilis* and therefore are more difficult to control to provide a final D.E. of 6 or less.

The level of alpha-amylase suitable for carrying out the present process is generally in the range of 0.1 to 0.6% based on starch solids when a commercial enzyme product such as the ones listed above is employed. The exact level employed will depend on the final D.E. desired, the enzyme activity and the temperature and pH of the reaction. If the final D.E. desired is in the range of 3–4, it is preferred to use a slightly higher temperature and pH, i.e. 97° C., pH 7.5, which requires a higher level of alpha-amylase to provide maximum filterability than would be required to obtain a 6 D.E. product at a lower temperature and pH, i.e. 95° C., pH 7.0. Usually for the preparation of hydrolyzates in the 4–6 D.E. range, we find that 0.2 to 0.4% alpha-amylase assaying 3,000 to 4,000 SKB units per gram gives satisfactory results.

The reaction time and temperature are closely related; i.e., within the relatively narrow temperature range that the invention may be carried out, an increase in temperature shortens the time to attain maximum filterability. For the preparation of products in the less than 6 D.E. range a reaction time of 20 minutes at 95° C. is usually sufficient to provide a filterable hydrolyzate, although the time may be as short as 5 minutes or as long as 40 minutes.

The hydrolyzates of the present invention are superior to non-waxy starch hydrolyzates of the prior art, primarily with respect to better solubility and clarity of aqueous solutions at comparable D.E. values below 6. Whereas non-waxy products of 6 D.E. and below of the prior art are virtually unfilterable, the new low D.E. hydrolyzates of the invention can be easily filtered and treated with carbon to provide products which are substantially completely soluble in water with the solutions being essentially colorless, odorless and tasteless. The hydrolyzates of the present invention have very low levels of the lower saccharides as shown by the data in Example 5. The clarity stability is substantially improved over products prepared by prior art processes as shown by the data in Example 4. The new low D.E. starch hydrolyzates may be characterized as follows:

1. A low D.E. of 6 or less.
2. Completely soluble in water at 80° C. at all solids concentrations below 35%.
3. Clarity of 30% solutions at 80° C. measured against water in a 19 millimeter cell at 600 m$\mu$ exceeds 60% light transmittance.
4. Contain less than 1.0% monosaccharide and less than 1.5% disaccharide and a descriptive ratio, calculated by dividing sum of DP1–DP6 saccharides by D.E., of less than 2.
5. Can be filtered at good filtration rates, i.e. at rates in excess of 100 milliliters per minute. (See Example 1.)

Thus, the invention provides a refined non-waxy starch hydrolyzate having a D.E. value of less than 6, said hydrolyzate being refined by treatment with carbon and filtering, and being substantially completely soluble in water at 80° C. at all solids concentrations below 35%, said hydrolyzate having a saccharide composition corresponding to the following:
Monosaccharides(DP1)Less than 0.4% by weight
Disaccharides(DP2)Less than 0.9% by weight
Trisaccharides(DP3)Less than 1.7% by weight
Tetrasaccharides(DP4)Less than 1.6% by weight
Pentasaccharides(DP5)Less than 1.4% by weight
Hexasaccharides(DP6)Less than 2.3% by weight
and a total content of DP1 through DP6 saccharides of less than about 8.2% by weight, dry basis, and a descriptive ratio of not more than 1.5, the descriptive ratio being the quotient obtained by dividing the sum of the percentages of saccharides having a degree of polymerization of 1 to 6 by the dextrose equivalent value.

The following examples further illustrate the invention and the advantages thereof.

EXAMPLE 1

Two 3-liter samples of acid-liquefied, non-waxy corn starch were obtained from a commercial jet cooker. The liquefied starch contained 25% solids, had a pH of 7.2 and a D.E. of 2.2. One sample was held at 80° C. and the other at 96° C. Bacterial alpha-amylase (Canalpna 180) was added to both samples at a level of 0.2% based on starch solids. This level was equivalent to 800 SKB units of alpha-amylase per 100 grams of starch. Two hundred milliliter portions were removed at 5, 10, 20, 30 and 40 minutes, acidified to pH 3.5–4.0, and checked for filterability by the following test:*

* This test method is used throughout to abtain data on filtration.

A 9 centimeter, jacketed, filtering funnel heated with circulating water at 80° C. was equipped with #1 Whatman filter paper and attached to an aspirator. Two grams of filteraid (Celatom) was added to 200 milliliters of crude hydrolyzate at 75°–77° C. and poured into the funnel. A stop watch was to measure the time to filter the entire sample or the volume filtered in 5 minutes. The filtration time was used to calculate the filtration rate in milliters per minute.

The results comparing alpha-amylase treatment at 80° and 96° C. are reported below. It is readily apparent that the rate of D.E. increase is much higher at 80° C. than at 96° C. while the filtration rate is much higher after amylase treatment at 96° C. than at 80° C.

| Treatment | | | | |
|---|---|---|---|---|
| Enzyme | Temperature | Time, Minutes | Filtration Rate ml/min. | D.E. |
| A. 0.2% Canalpha | 80° C. | 0 | 5 | (2.2) |
| | | 5 | 13 | — |
| | | 10 | 16 | 6.6 |

-continued

| Treatment | | | | |
|---|---|---|---|---|
| Enzyme | Temperature | Time, Minutes | Filtration Rate ml/min. | D.E. |
|  |  | 20 | 31 | 9.3 |
|  |  | 30 | 26 | 11.7 |
|  |  | 40 | 31 | 13.7 |
| B. 0.2% Canalpha | 96° C. | 5 | 92 | 4.7 |
|  |  | 10 | 98 | 5.6 |
|  |  | 20 | 104 | 4.5 |
|  |  | 30 | 128 | 4.6 |
|  |  | 40 | 133 | 5.0 |

EXAMPLE 2

A six-liter sample of acid-liquefied starch, 23.3% solids, was obtained from a production jet cooker and divided into two 3-liter samples for treatment with Biocon Canalpha 180 alpha-amylase as shown below. One sample was held at 80° C. and the other at 95° C. Samples were removed periodically for measurements of D.E. and filterability after adjusting to pH 3.5–4.0 to inactivate enzyme.

| | Treatment | | | | Filtration | |
|---|---|---|---|---|---|---|
| No. | Enzyme | pH | Temperature °C. | Time Minutes | Rate ml/min. | D.E. |
| 1 | 0.2% Canalpha | 7.2 | 80 | 0 | | |
|  | " | " | " | 10 | 74 | 6.0 |
|  | " | " | " | 20 | 87 | 7.8 |
|  | " | " | " | 30 | 148 | 11.2 |
|  | " | " | " | 40 | 200 | 12.5 |
|  | " | " | " | 50 | 200 | 14.2 |
| 2 | 0.2% Canalpha | 7.2 | 95 | 10 | 92 | 2.8 |
|  | " | " | " | 20 | 114 | 3.4 |
|  | " | " | " | 30 | 148 | 4.5 |
|  | " | " | " | 40 | 120 | 5.6 |
|  | " | " | " | 50 | 156 | 5.9 |

The results show that the D.E. increased fastest in the 80° C. sample; however, the filtration rate increased faster at 95° C.

EXAMPLE 3

A dispersion of non-waxy starch was treated with alpha-amylase and liquefied in a commercial jet cooker. Two samples of liquefied starch were adjusted to pH 7.0 and heated to 80° C. and 95° C. for treatment with alpha-amylase as follows:

| | Treatment | | | | Filtration | |
|---|---|---|---|---|---|---|
| No. | Enzyme | pH | Temperature °C. | Time Minutes | Rate ml/min. | D.E. |
| 1 | 0.3% Canalpha | 7.0 | 80 | 0 | 20 | 2.59 |
|  | " | " | " | 5 | 81 | 5.88 |
|  | " | " | " | 10 | 92 | 8.29 |
|  | " | " | " | 20 | 270 | 11.29 |
|  | " | " | " | 30 | 88 | 14.37 |
|  | " | " | " | 40 | 240 | 16.4 |
| 2 | 0.3% Canalpha | 7.0 | 95 | 5 | 133 | 4.34 |
|  | " | " | " | 10 | 83 | 5.00 |
|  | " | " | " | 20 | 166 | 5.27 |
|  | " | " | " | 30 | 160 | 5.59 |
|  | " | " | " | 40 | 110 | 6.01 |

The results show that D.E. increased faster at 80° C. than at 95° C. while the filtration rate for the low D.E. products (<6) was much faster using a 95° reaction temperature than at 80° C. For example, at 80° the D.E. reached 5.88 after 5 minutes and provided a filtration rate of 81 milliliters per minute. At 95° the D.E. reached 5.6 at 30 minutes and had a filtration rate of 160 milliliters per minute.

EXAMPLE 4

Four 3-liter samples of acid-liquefied starch were drawn from a commercial, steam jet cooker. The liquefied starch contained 22% solids and had a D.E. of 2.2. The pH was adjusted to 7.2 and the temperature held at 85, 90, 95 and 99° C. as shown below. Alpha-amylase (Biocon Canalpha 180) was added at a level of 0.3% based on solids. Samples were removed periodically, acidified with hydrochloric acid to pH 4 and tested for filterability using the Standard Filtration Test described previously. A portion of the filtrate was used to determine D.E. and checked for clarity after heating to 80° C., then cooling to 60° C. Clarity was determined by measuring the light transmittance against water at 600 m$\mu$ using a 19 millimeter B&L test tube in a Spectronic 20 Colorimeter The results are given in the table below. The data show that treatment with alpha-amylase at temperatures of 95° or 99° C. produced filtrable hydrolyzates in the 3–5 D.E. range while at 85° filtrable products were not obtained until the D.E. reached 6 or 7. The clarity data show that increasing the temperature of amylase treatment from 85° to 9° produced a substantial improvement in clarity stability of samples in the 3–6 D.E. range.

| | Enzyme Treatment | | | | Clarity (% T) | | Iodine Absorption |
|---|---|---|---|---|---|---|---|
| Series | Temperature °C. | Time, minutes | Filtration Rate ml/min. | D.E. | 80° C. | 60° C. | Value |
| A | 85 | 0 | Negligible | | | | |
|  | " | 5 | 63 | 6.39 | 44 | 5 | 16.9 |
|  | " | 10 | 167 | 7.13 | 75 | 48 | 8.2 |
|  | " | 20 | 312 | 10.2 | 90 | 50 | 3.3 |
|  | " | 30 | 312 | 13.0 | 90 | 56 | |
|  | " | 40 | 400 | 15.5 | 95 | 67 | |
| B | 90 | 5 | 93 | 4.46 | 69 | 2 | |
|  | " | 10 | 112 | 7.96 | 90 | 60 | |
|  | " | 20 | 114 | 8.46 | 91 | 70 | |
|  | " | 30 | 114 | 10.4 | 94 | 78 | |
|  | " | 40 | 298 | 12.6 | 94 | 84 | |
| C | 95 | 5 | 138 | 3.68 | 59 | 2 | 20.5 |
|  | " | 10 | 177 | 4.60 | 68 | 9 | 15.5 |
|  | " | 20 | 238 | 6.55 | 84 | 45 | 7.8 |
|  | " | 30 | 210 | 7.06 | 83 | 80 | |
|  | " | 40 | 182 | 7.72 | 86 | 80 | |
| D | 99 | 5 | 109 | 2.83 | 49 | 0 | |

-continued

| Series | Enzyme Treatment Temperature °C. | Time, minutes | Filtration Rate ml/min. | D.E. | Clarity (% T) 80° C. | 60° C. | Iodine Absorption Value |
| --- | --- | --- | --- | --- | --- | --- | --- |
| | " | 10 | 95 | 3.14 | 57 | 1 | 47.8 |
| | " | 20 | 92 | 3.06 | 66 | 2 | 46.4 |
| | " | 30 | 117 | 5.00 | 82 | 8 | 14.2 |
| | " | 40 | 154 | 5.11 | 82 | 12 | |

EXAMPLE 5

Several samples of non-waxy hydrolyzates with D.E.'s between 4 and 6 were prepared by the process of the invention and analyzed for D.E. and saccharide profile as shown in the following table:

the relative reducing values for the $DP_1$ through $DP_6$ polymers as determined by Commerford and Scallet, Cereal Chem. 46 172 (1969).

The results are shown below:

| Sample | D.E. | Saccharide Composition, % By Weight DP1 | DP2 | DP3 | DP4 | DP5 | DP6 | DP7 % Higher | Total DP1-6 | Descriptive Ratio | Average M.W. DP7 & Higher |
| --- | --- | --- | --- | --- | --- | --- | --- | --- | --- | --- | --- |
| F | 4.6 | 0.2 | 0.6 | 0.9 | 0.9 | 0.7 | 1.0 | 95.7 | 4.3 | 0.9 | 5,700 |
| G | 5.1 | 0.2 | 0.6 | 1.1 | 1.0 | 0.8 | 1.1 | 95.2 | 4.8 | 0.9 | 4,900 |
| H | 4.7 | 0.2 | 0.6 | 0.9 | 0.8 | 0.7 | 1.0 | 95.8 | 4.2 | 0.9 | 5,530 |
| I | 5.1 | 0.3 | 0.6 | 1.0 | 0.9 | 0.7 | 1.1 | 95.4 | 4.6 | 0.9 | 5,044 |
| J | 5.0 | 0.2 | 0.7 | 1.1 | 0.9 | 0.6 | 1.0 | 95.5 | 4.5 | 0.9 | 5,044 |
| K | 5.4 | 0.1 | 0.5 | 1.1 | 0.9 | 0.7 | 1.1 | 95.6 | 4.4 | 0.8 | 4,396 |
| L | 4.5 | 0.3 | 0.7 | 0.9 | 0.8 | 0.6 | 0.9 | 95.8 | 4.2 | 0.9 | 6,100 |
| M | 4.2 | 0.2 | 0.6 | 1.1 | 1.0 | 0.6 | 0.8 | 95.7 | 4.3 | 1.0 | 6,666 |
| N | 4.5 | 0.2 | 0.9 | 1.2 | 1.2 | 1.2 | 1.6 | 93.7 | 6.3 | 1.4 | 7,152 |
| O | 4.6 | 0.1 | 016 | 1.2 | 1.2 | 1.1 | 1.8 | 94.0 | 6.0 | 1.3 | 6,260 |
| P | 5.2 | 0.3 | 0.9 | 1.4 | 1.3 | 1.3 | 1.9 | 92.9 | 7.1 | 1.4 | 4,600 |
| Q | 5.1 | 0.2 | 0.7 | 1.0 | 1.0 | 1.0 | 1.5 | 94.6 | 5.4 | 1.1 | 5,210 |
| R | 5.7 | 0.3 | 1.1 | 1.6 | 1.5 | 1.4 | 2.1 | 92.0 | 8.0 | 1.4 | 5.750 |

| Sample No. | D.E. | Saccharide Profile DP1 | DP2 | DP3 | DP4 | DP5 | DP6 | Over DP6 | Descriptive Ratio* |
| --- | --- | --- | --- | --- | --- | --- | --- | --- | --- |
| A | 4.1 | 0.12 | 0.46 | 0.81 | 0.80 | 0.79 | 1.11 | 95.9 | 1.0 |
| B | 5.9 | 0.4 | 0.8 | 1.7 | 1.6 | 1.4 | 2.3 | 91.8 | 1.4 |
| C | 4.0 | 0.3 | 0.6 | 1.0 | | | | | |
| D | 4.6 | 0.8 | 1.3 | 1.3 | | | | | |
| E | 4.5 | 0.2 | 0.3 | 0.2 | | | | | |

*Descriptive Ratio: Sum of saccharides from DP1 through DP6 divided by D.E.

EXAMPLE 6

Additional samples of non-waxy hydrolyzates with D.E.'s below 6 were prepared by the process of the invention and analyzed for D.E. and saccharide profile. In addition, the average molecular weights of the glucose polymers (or the average reducing value) of the DP7 and above fractions were calculated.

The average molecular weights were calculated as follows:

$$MW_{DP_7 \to} = \frac{180.16}{\text{Relative Reducing Value, } DP_{7 \to}}$$

$$\text{Rel. Red. Value, } DP_{7 \to} = \frac{DE \text{ sample} - DE \text{ Contribution, } DP_{1-6}}{\% DP_{7 \to}}$$

$$DE \text{ contribution,} = (\% DP_1 \times 1.0 + \% DP_2 \times 0.58 + \% DP_3 \times 0.395 + \% DP_4 \times 0.30 + \% DP_5 \times 0.242 + \% DP_6 \times 0.208)$$

where DE sample=Dextrose equivalent of sample obtained by reducing sugar determination and %$DP_1$, %$DP_2$, etc. is the percentage by weight, dry basis, of the glucose, maltose, triose, etc., as determined by HPLC analysis. The constants 1.0, 0.58, 0.395, etc. are

EXAMPLE 7

Three liters of acid-cooked starch paste from a production steam jet cooker were adjusted to pH 7.0 with sodium carbonate and cooled to 96° C. Forty-eight milliliters of diluted Biocon Canalpha bacterial alpha-amylase (equal to 0.4% on starch dry substance) were added and the solution held at 95°-96° C. for 27 minutes. Hydrochloric acid was added to adjust the pH to 4.2 and 2.5 grams carbon added. After 10 minutes at 95° C., the solution was cooled to 85° C. and filtered with the aid of a filter aid. The filtrate was water-clear at temperatures above 75° C. and had a D.E. of 4.3.

Those modifications and equivalents which fall within the spirit of the invention are to be considered a part thereof.

What is claimed is:

1. A starch hydrolyzate product produced by the process which comprises treating an aqueous slurry of non-waxy starch with an acid or enzyme to liquefy the starch and to provide an aqueous dispersion substantially free of residual starch granules with a measurable dextrose equivalent value of up to about 3, then treating said dispersion with a bacterial alpha-amylase at a temperature from about 95° C. to 100° C. and a pH of from about 6.5 to 8 to produce said starch hydrolyzate product having a measurable dextrose equivalent value of up to about 7.72, stopping said bacterial alpha-amylase action and recovering said starch hydrolyzate having a measurable dextrose equivalent value of up to about 7.72.

2. A starch hydrolyzate product in accordance with claim 1 wherein said treatment with said bacterial alpha-amylase is carried out at a pH of from about 6.8 to 7.5.

3. A starch hydrolyzate product in accordance with claim 1 wherein said recovered starch hydrolyzate product has a measurable dextrose equivalent value up to about 6.

4. A starch hydrolyzate product in accordance with claim 1 wherein said starch hydrolyzate product is recovered by filtration.

5. A starch hydrolyzate product in accordance with claim 1 wherein said starch hydrolyzate product is recovered by filtration and then treated with carbon to obtain a refined starch hydrolyzate product.

* * * * *